United States Patent
Hershgold et al.

(10) Patent No.: US 9,028,498 B2
(45) Date of Patent: May 12, 2015

(54) MODULAR BONE FIXATION PLATE ASSEMBLY

(71) Applicant: Innovasis, Inc., Salt Lake City, UT (US)

(72) Inventors: David A. Hershgold, Draper, UT (US); Brent A. Felix, Sandy, UT (US)

(73) Assignee: Innovasis, Inc., Salt Lake City, UT (US)

( * ) Notice: Subject to any disclaimer, the term of this patent is extended or adjusted under 35 U.S.C. 154(b) by 121 days.

(21) Appl. No.: 13/829,597

(22) Filed: Mar. 14, 2013

(65) Prior Publication Data
US 2014/0276829 A1 Sep. 18, 2014

(51) Int. Cl.
*A61B 17/80* (2006.01)
*A61B 17/70* (2006.01)

(52) U.S. Cl.
CPC ......... *A61B 17/7059* (2013.01); *A61B 17/8023* (2013.01); *A61B 17/8042* (2013.01)

(58) Field of Classification Search
CPC .................................................. A61B 17/8023
USPC .................................................. 606/71, 289
See application file for complete search history.

(56) References Cited

U.S. PATENT DOCUMENTS

| | | |
|---|---|---|
| 5,520,690 A | 5/1996 | Errico et al. |
| 5,531,746 A | 7/1996 | Errico et al. |
| 5,531,747 A | 7/1996 | Ray |
| 5,616,142 A | 4/1997 | Lin |
| 5,643,265 A | 7/1997 | Errico et al. |
| 5,681,313 A | 10/1997 | Diez |
| 5,964,763 A | 10/1999 | Beynnon |
| 6,139,316 A | 10/2000 | Frazin-Nia |
| 7,938,848 B2 | 5/2001 | Sweeney |
| 6,402,756 B1 | 6/2002 | Ralph et al. |
| 6,585,738 B1 | 7/2003 | Mangione et al. |
| 6,599,290 B2 | 7/2003 | Bailey et al. |
| 6,689,134 B2 | 2/2004 | Ralph et al. |
| 6,755,833 B1 | 6/2004 | Paul et al. |
| 6,945,974 B2 | 9/2005 | Dalton |
| 6,945,975 B2 | 9/2005 | Dalton |
| 6,979,334 B2 | 12/2005 | Dalton |
| 7,008,426 B2 | 3/2006 | Paul |
| 7,041,105 B2 | 5/2006 | Michelson |
| 7,044,952 B2 | 5/2006 | Michelson |
| 7,070,599 B2 | 7/2006 | Paul |
| 7,097,645 B2 | 8/2006 | Michelson |
| 7,112,202 B2 | 9/2006 | Michelson |

(Continued)

FOREIGN PATENT DOCUMENTS

| | | |
|---|---|---|
| CN | 100435743 | 11/2008 |
| WO | 02/098276 | 12/2002 |

(Continued)

*Primary Examiner* — David Bates

(57) ABSTRACT

A bone fixation plate assembly includes a proximal plate having a proximal body with a first arm projecting therefrom, the first arm having an elongated expansion slot extending through a portion thereof and a threaded bore formed thereon so as to communicate with the expansion slot. A set screw is received within the threaded bore and has a top surface with a driver engaging feature formed thereon and an encircling perimeter edge. A distal plate has a distal body with a first sleeve projecting therefrom. The first sleeve bounds a socket with the first arm received therein. An access opening is formed on the first sleeve and is configured so that the driver engaging feature of the set screw is accessible through the access opening while at least a portion of the perimeter edge of the set screw is covered by the first sleeve.

20 Claims, 14 Drawing Sheets

(56) References Cited

U.S. PATENT DOCUMENTS

| | | |
|---|---|---|
| 7,115,130 B2 | 10/2006 | Michelson |
| 7,118,573 B2 | 10/2006 | Michelson |
| 7,135,024 B2 | 11/2006 | Cook et al. |
| 7,186,254 B2 | 3/2007 | Dinh |
| 7,186,256 B2 | 3/2007 | Michelson |
| 7,214,226 B2 | 5/2007 | Alleyne |
| 7,278,997 B1 | 10/2007 | Mueller et al. |
| 7,306,605 B2 | 12/2007 | Ross |
| 7,311,712 B2 | 12/2007 | Dalton |
| 7,318,825 B2 | 1/2008 | Butler et al. |
| 7,331,961 B2 | 2/2008 | Abdou |
| 7,476,228 B2 | 1/2009 | Abdou |
| 7,527,640 B2 | 5/2009 | Ziolo et al. |
| 7,591,840 B2 | 9/2009 | Suddaby |
| 7,604,638 B2 | 10/2009 | Jacene et al. |
| 7,635,364 B2 | 12/2009 | Barrall et al. |
| 7,641,675 B2 | 1/2010 | Lindemann et al. |
| 7,682,362 B2 | 3/2010 | Dees, Jr. |
| 7,727,265 B2 | 6/2010 | Paul |
| 7,727,266 B2 | 6/2010 | Lindemann et al. |
| 7,740,630 B2 | 6/2010 | Michelson |
| 7,749,256 B2 | 7/2010 | Farris et al. |
| 7,763,056 B2 | 7/2010 | Dalton |
| 7,794,482 B2 | 9/2010 | Mathieu et al. |
| 7,803,157 B2 | 9/2010 | Michelson |
| 7,811,285 B2 | 10/2010 | Michelson |
| 7,815,666 B2 | 10/2010 | Baynham et al. |
| 7,887,570 B2 | 2/2011 | Ziolo et al. |
| 7,931,678 B2 | 4/2011 | Konieczynski et al. |
| 7,942,913 B2 | 5/2011 | Ziolo et al. |
| 7,951,151 B2 | 5/2011 | Butler et al. |
| 7,951,178 B2 | 5/2011 | Jensen |
| 7,955,364 B2 | 6/2011 | Ziolo et al. |
| 7,998,179 B2 | 8/2011 | Lindemann et al. |
| 8,002,809 B2 | 8/2011 | Baynham |
| 8,002,810 B2 | 8/2011 | Osman |
| 8,048,131 B2 | 11/2011 | Dalton |
| 8,070,749 B2 | 12/2011 | Stern |
| 8,123,785 B2 | 2/2012 | Weaver et al. |
| 8,128,628 B2 | 3/2012 | Freid et al. |
| 8,128,668 B2 | 3/2012 | Paul |
| 8,182,518 B2 | 5/2012 | Butler et al. |
| 8,187,329 B2 | 5/2012 | Theofilos |
| 8,206,390 B2 | 6/2012 | Lindemann |
| 8,211,145 B2 | 7/2012 | Dalton |
| 8,231,662 B2 | 7/2012 | Huebner |
| 8,262,710 B2 | 9/2012 | Freedman et al. |
| 8,262,711 B2 | 9/2012 | Hess |
| 8,262,713 B2 | 9/2012 | Attawia et al. |
| 8,282,675 B2 | 10/2012 | Maguire et al. |
| 8,298,271 B2 | 10/2012 | Jacene et al. |
| 8,328,854 B2 | 12/2012 | Baynham et al. |
| 8,348,949 B2 | 1/2013 | Butler et al. |
| 8,357,181 B2 | 1/2013 | Lange et al. |
| 8,361,130 B2 | 1/2013 | Daly et al. |
| 8,372,123 B2 | 2/2013 | Smisson, III et al. |
| 8,382,842 B2 | 2/2013 | Greenhalgh et al. |
| 8,388,663 B2 | 3/2013 | Bush, Jr. et al. |
| 8,419,776 B2 | 4/2013 | Prandi et al. |
| 2005/0234452 A1* | 10/2005 | Malandain ............... 606/61 |
| 2008/0065070 A1* | 3/2008 | Freid et al. ............... 606/61 |
| 2008/0140129 A1 | 6/2008 | Dalton |
| 2009/0299370 A1 | 12/2009 | Kiester |
| 2010/0121328 A1* | 5/2010 | Reitzig et al. ............ 606/71 |

FOREIGN PATENT DOCUMENTS

| | | |
|---|---|---|
| WO | 03/000148 | 1/2003 |
| WO | 03/063714 | 8/2003 |
| WO | 2004/008978 | 1/2004 |
| WO | 2005/009259 | 2/2005 |
| WO | 2005/018419 | 3/2005 |

* cited by examiner

MODULAR BONE FIXATION PLATE ASSEMBLY

CROSS-REFERENCE TO RELATED APPLICATIONS

Not applicable.

BACKGROUND OF THE INVENTION

1. The Field of the Invention

The present invention relates to modular bone fixation plate assemblies and, more specifically, modular spinal plate assemblies used for securing together adjacent vertebrae of the spine.

2. The Relevant Technology

Bone fixation plate assemblies are used for securing together adjacent bones or bone segments. For example, bone fixation plate assemblies are commonly used for securing together adjacent vertebra of the spine when it is desired to fuse the vertebra together. U.S. Pat. No. 6,402,756 discloses one type of bone fixation plate assembly. As depicted in FIG. 1, the plate assembly 9 includes a first plate 1A having a first pair of through holes 2A and 2B for receiving bone screws and a pair of prongs 3A and 3B. A threaded bore 4 is formed at the intersection between prongs 3A and 3B and is configured to receive a set screw (not shown). Plate assembly 9 also includes a second plate 1B that has a second pair of through holes 4A and 4B for receiving bone screws and an end face with an elongated bore 5 formed therein and configured to receive the pair of prongs 3A and 3B. An opening 6 is formed on a top surface of second plate 1B so that when prongs 3A and 3B are received within bore 5, threaded bore 4 can be accessed through opening 6.

During use, prongs 3A and 3B are slidably received within bore 5 and are advanced or retracted therein until plate assembly 9 achieves a desired length for mounting on adjacent bones. The set screw is then threaded into threaded bore 4 through opening 6. As set screw is screwed into threaded bore 4, prongs 3A and 3B are pushed apart so as to bias against the interior surface of second plate 1B, thereby securing first plate 1A to second plate 1B by frictional engagement. Plate assembly 9 can then be placed to span between two bones and the bone screws can be passed through holes 2A, 2B and 4A, 4B and into the bones so that plate assembly 9 is secured to the adjacent bones.

Although plate assembly 9 is functional, it has a number of shortcomings. For example, plate assembly 9 can only be used for securing two adjacent bones together. It is common, however, to fuse together three or more consecutive vertebra. In that case two or more separate plate assemblies 9 is required where the end of two separate plate assemblies needs to be screwed into the same vertebra. Attaching multiple separate plates is labor intensive and time consuming. It addition, it can often be difficult to attach four separate bone screws to a single vertebra or other bone, especially where the bone is weak or damaged.

Furthermore, in plate assembly 9 the set screw threaded into bore 4 is openly exposed when plate assembly 9 is implanted within a patient. As such, if the set screw ever becomes loose, it could separate from plate assembly 9 and become a potential hazard to the patient. A second surgical procedure would then be required to retrieve the set screw.

In addition, plate assembly 9 fully covers the bone portions over which plate assembly 9 is placed. For many surgeons this can be problematic in that they want to see portions of the underlying bone(s) or biologic fusion material to ensure that plate assembly 9 is optimally positioned.

Accordingly, what is needed in the art are bone fixation plate assemblies that address some or all of the above shortcomings.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements. Furthermore, multiple instances of an element may each include separate letters appended to the element number. For example two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

DETAILED DESCRIPTION OF THE PREFERRED EMBODIMENTS

Figure 1:
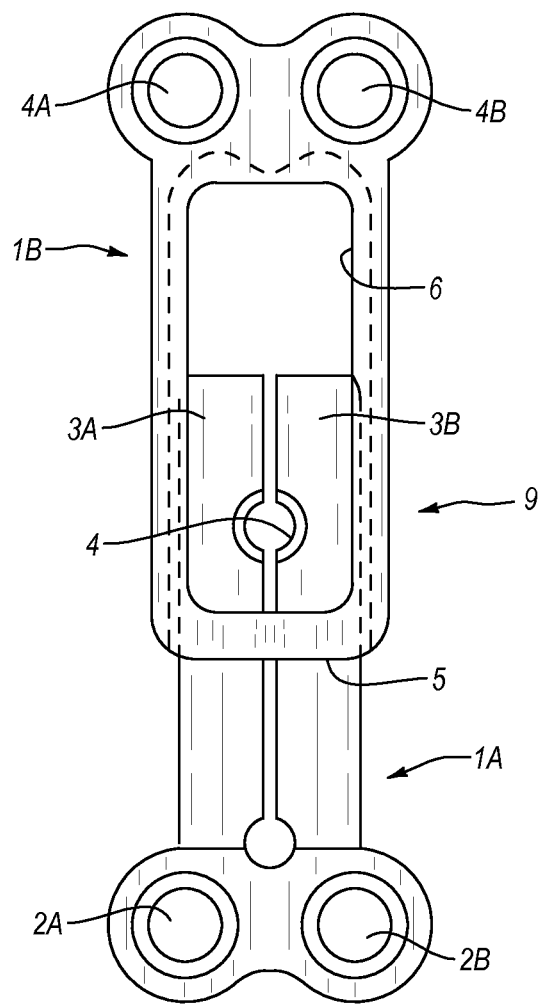
FIG. 1 is a top plan view of a prior art bone fixation plate assembly.

In the following detailed description, reference is made to the accompanying drawings, which form a part hereof. In the drawings, similar symbols typically identify similar components, unless context dictates otherwise. The embodiments described in the detailed description, drawings, and claims are not meant to be limiting. Other embodiments may be utilized, and other changes may be made, without departing from the spirit or scope of the subject matter presented herein.

It will be readily understood that the aspects of the present disclosure, as generally described herein, and illustrated in the figures, can be arranged, substituted, combined, separated, and designed in a wide variety of different configurations, all of which are explicitly contemplated herein. It will also be understood that any reference to a first, second, etc. element in the claims or in the detailed description, is not meant to imply numerical sequence, but is meant to distinguish one element from another unless explicitly noted as implying numerical sequence.

In addition, as used in the specification and appended claims, directional terms, such as "top," "bottom," "up," "down," "upper," "lower," "proximal," "distal," "horizontal," "vertical," and the like are used herein solely to indicate relative directions and are not otherwise intended to limit the scope of the invention or claims.

Figure 2:
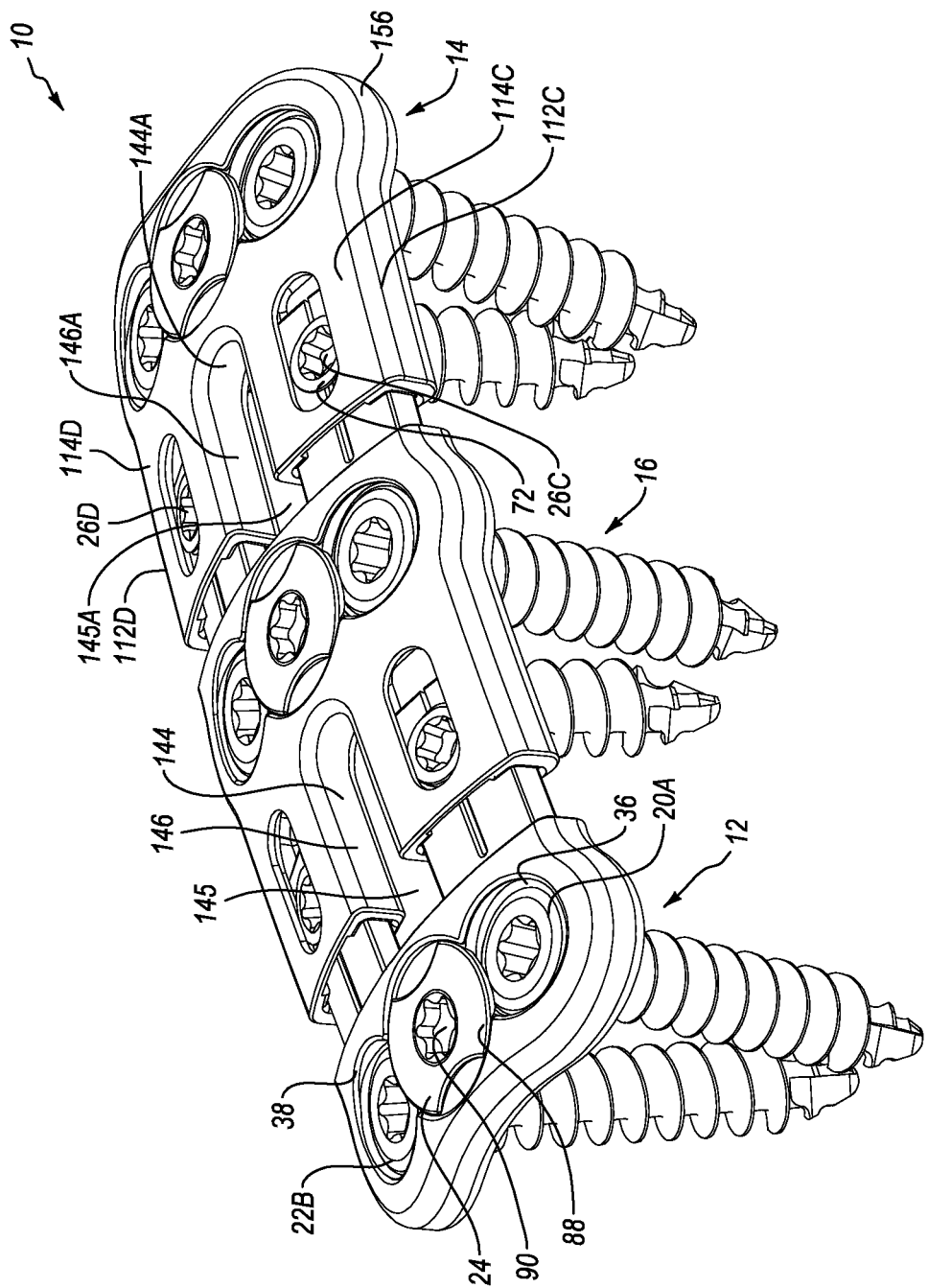
FIG. 2 is a perspective view of a bone fixation plate assembly incorporating features of the present invention.

Depicted in FIG. 2 is one embodiment of an inventive bone fixation plate incorporating features of the present invention. In one embodiment, bone fixation plate assembly 10 can comprise a cervical plate assembly used for fixing together adjacent vertebrae of the cervical portion of the spine. In other embodiments, bone fixation plate assembly 10 can be modified or sized to be used for fixing together other vertebra of the spine or other bones or sections of a bone that are not part of the spine.

In general, bone fixation plate assembly 10 comprises a proximal plate assembly 12, a distal plate assembly 14, and a central plate assembly 16 disposed between plate assembles 12 and 14. As used in the specification and appended claims, it is again noted that the terms "proximal" and "distal" are arbitrary names that are simply used to differentiate between the different plate assemblies and the components of the different plate assemblies. The terms are not intended to otherwise limit or define the invention.

Figure 3:
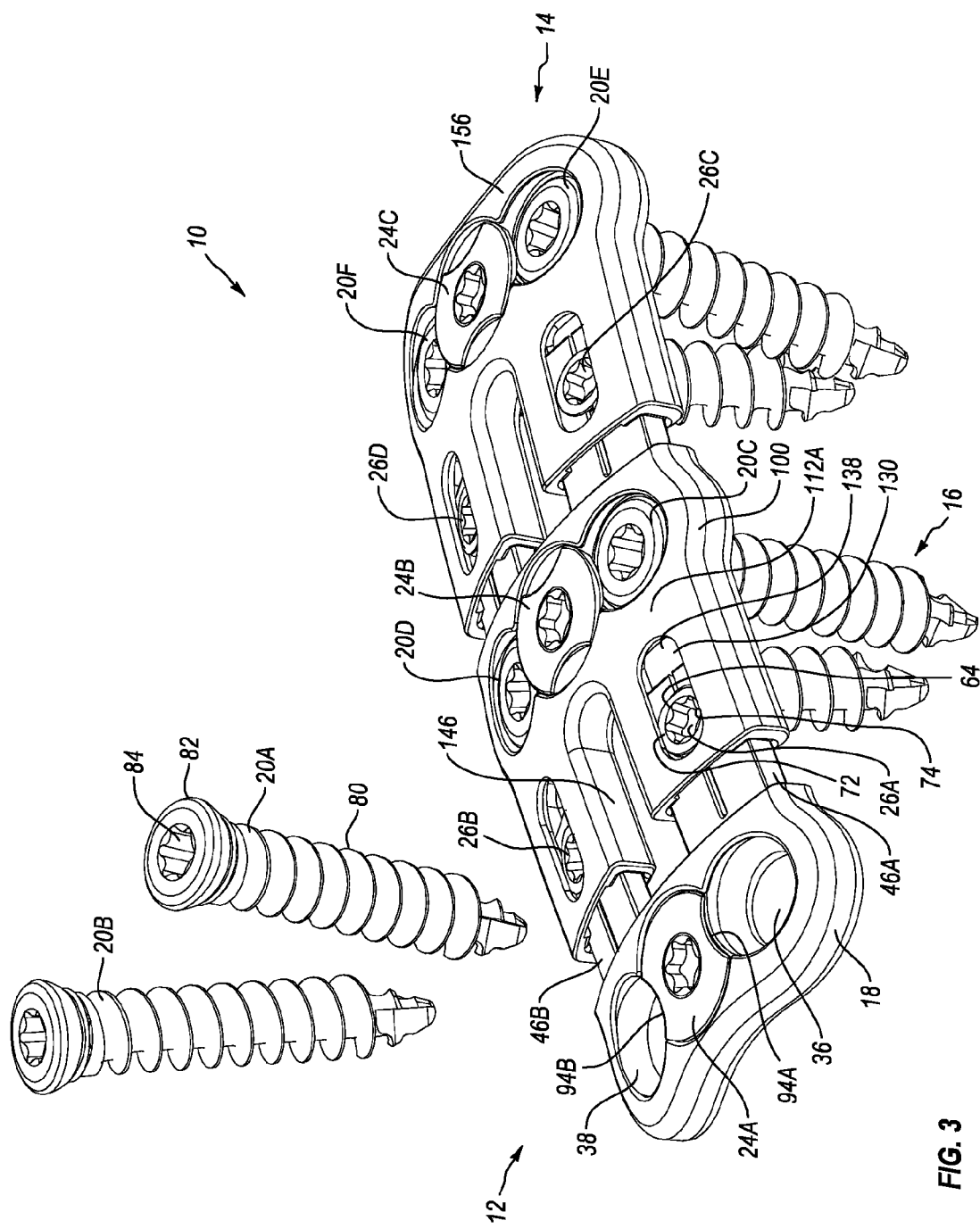
FIG. 3 is a partially exploded perspective view of the plate assembly shown in FIG. 2.

As depicted in FIG. 3, proximal plate assembly 12 comprises a proximal plate 18 that can be selectively secured to a bone, such as a vertebra, by first and second proximal bone screws 20A and 20B, respectively. Rotatably coupled to proximal plate 18 is a locking element 24A and first and second proximal set screws 26A and 26B.

Figure 4:
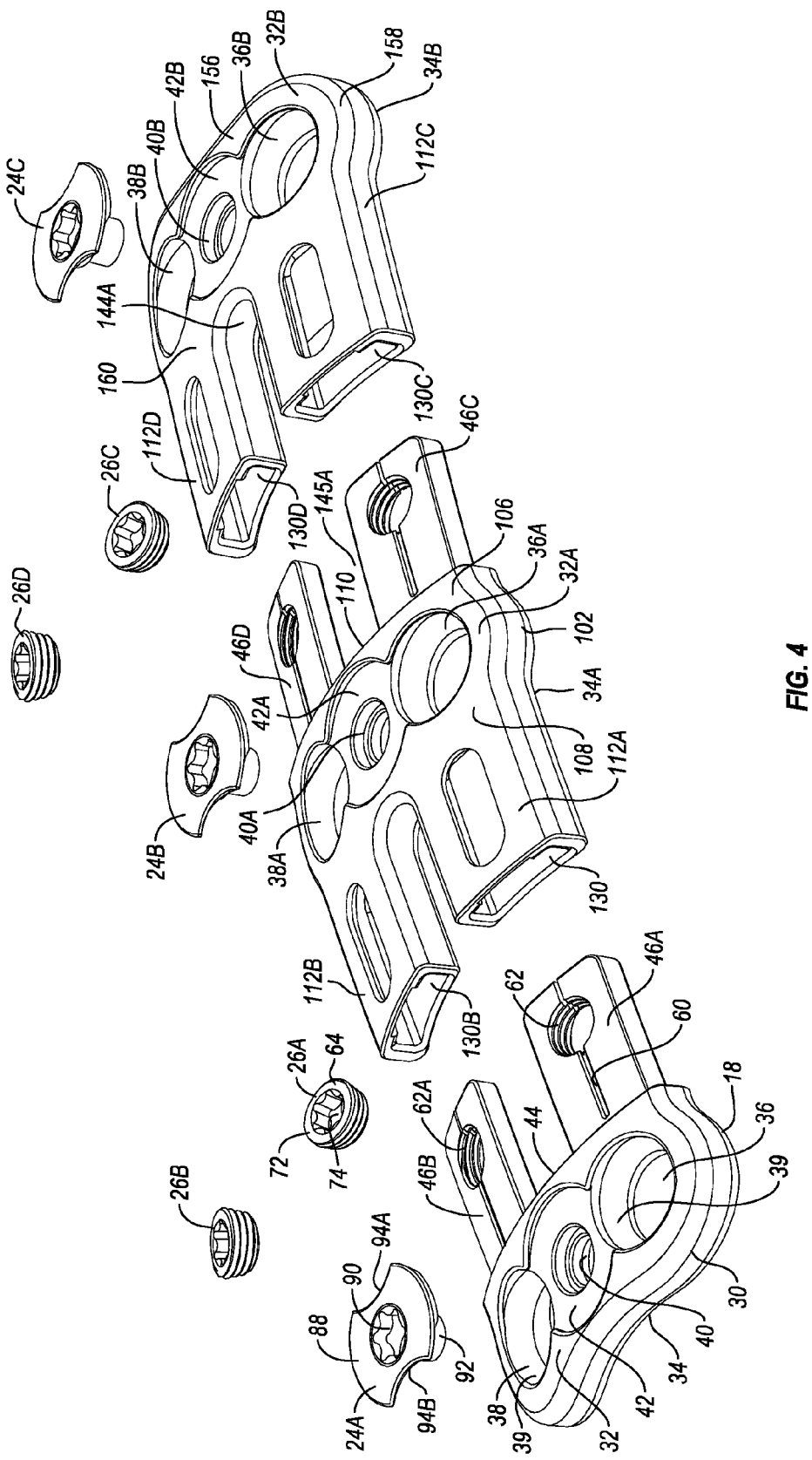
FIG. 4 is a fully exploded view of the plate assembly shown in FIG. 2 without the bone screws.
Figure 5:
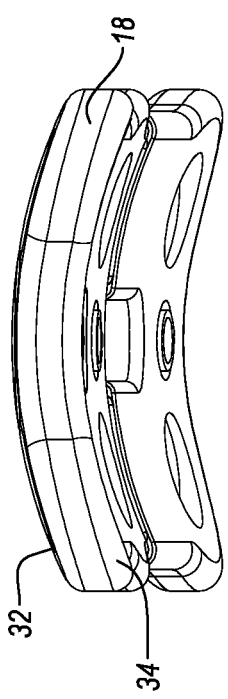
FIG. 5 is an end view of the assembled plates of the plate assembly shown in FIG. 3.
Figure 6:
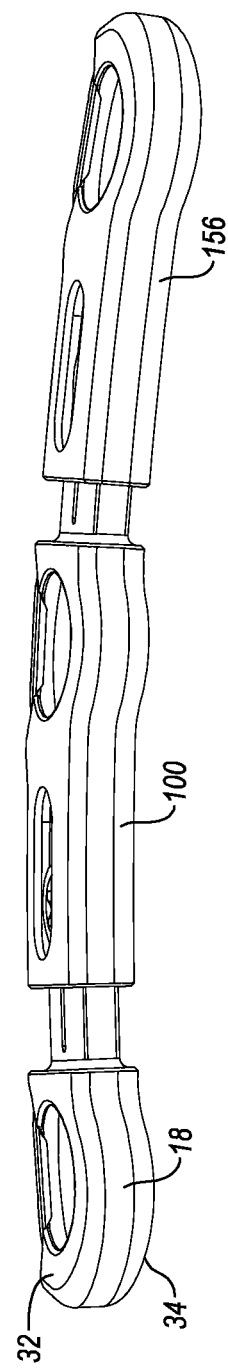
FIG. 6 is an elevated side view of the assembled plates shown in FIG. 5.
Figure 11:
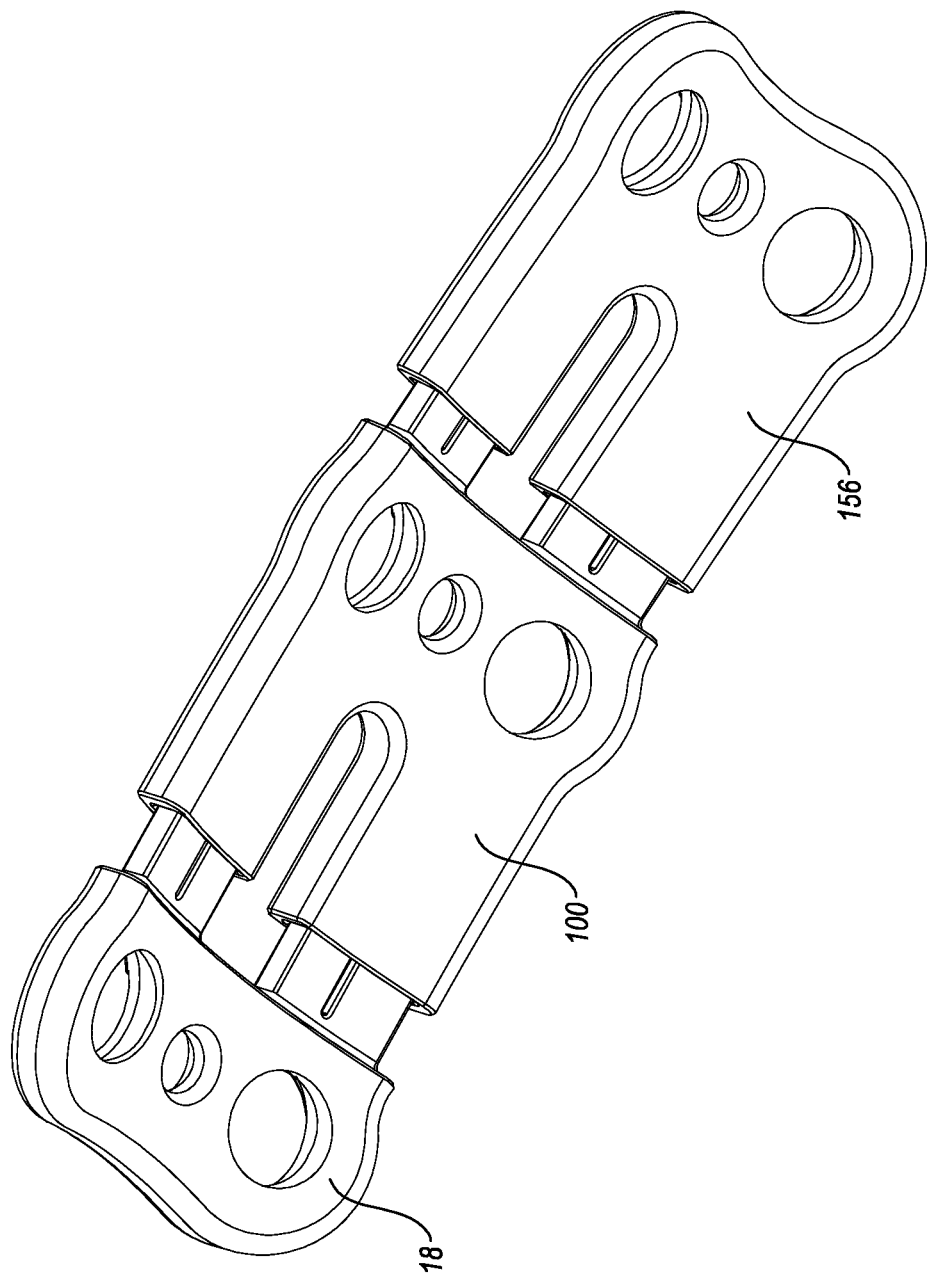
FIG. 11 is a bottom perspective view of the assembled plates shown in FIG. 6.

Turning to FIG. 4, proximal plate 18 comprises a proximal body 30 having a top surface 32 and an opposing bottom surface 34. Proximal plate 18 has a compound curvature. That is, bottom surface 34 of proximal plate 18 has a concave curvature extending from side to side as depicted in FIGS. 5 and 11 and a concave curvature extending from end to end as depicted in FIGS. 5 and 6. Likewise, top surface 32 of proximal plate 18 has a complementary convex curvature extending from side to side as depicted in FIGS. 5 and 11 and complementary convex curvature extending from end to end as depicted in FIGS. 5 and 6. These curvatures assist in the placement of bone fixation plate 10 across adjacent vertebrae of the cervical portion of the spine. In alternative embodiments, however, it is appreciated that bone fixation plate assembly 10 can be used in other locations on or off the spine and in those configurations proximal plate 18 can be flat or have other desired curvatures.

Returning to FIG. 4, first and second proximal bone screw holes 36 and 38 extend through proximal body 30 from top surface 32 to bottom surface 34. Proximal bone screw holes 36 and 38 have an interior surface 39 that inwardly tapers toward bottom surface 34 so that the heads of bone screws 20A and 20B can be pivotally retained therein. A lock hole 40 also passes through proximal body 30 between top surface 32 and bottom surface 34 at a central location between bone screw holes 36 and 38. An annular recess 42 is formed on top surface 32 so as to encircle lock hole 40. Recess 42 is adapted to receive locking element 24A as will be discussed below in great detail.

Figure 7:
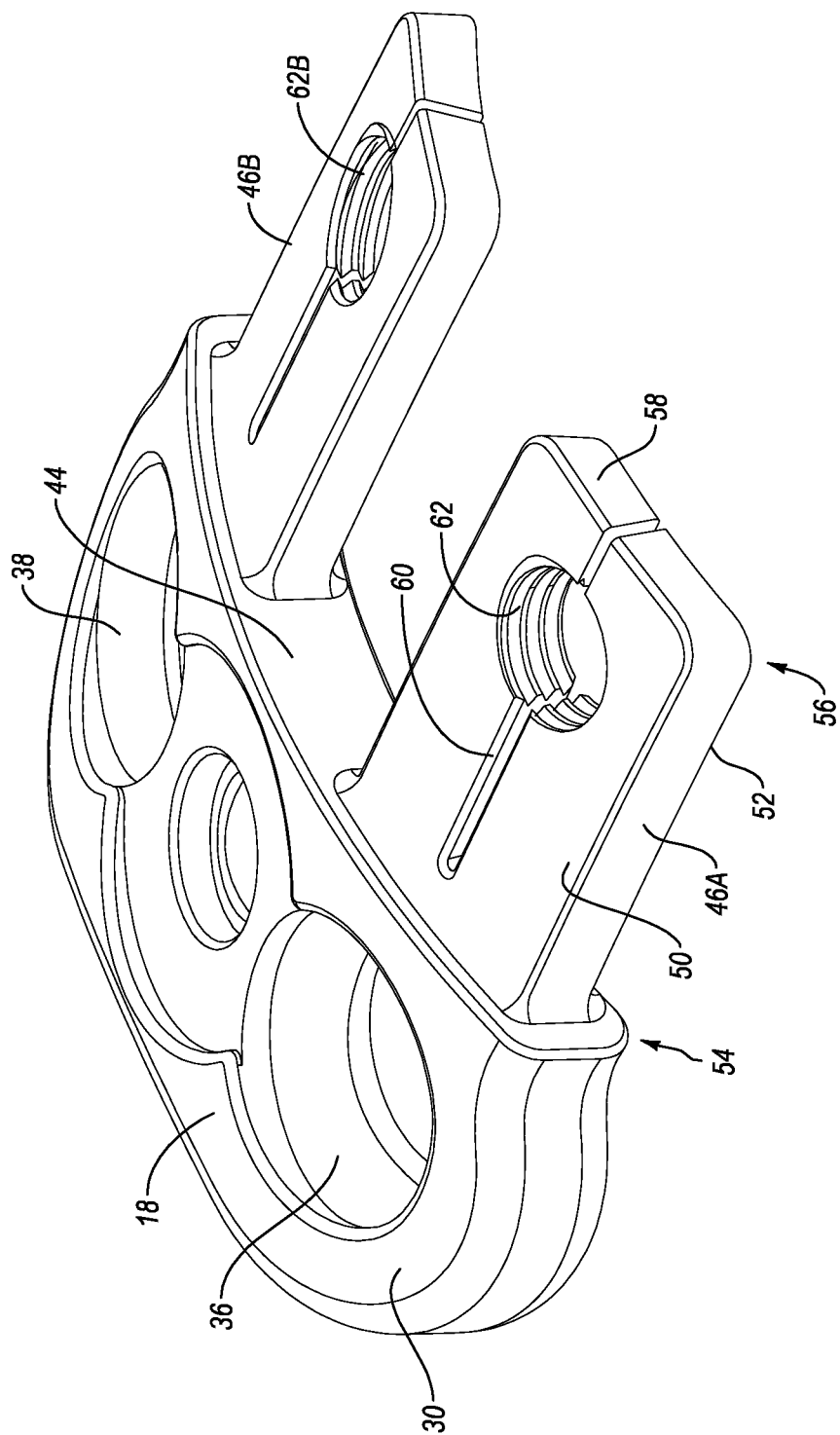
FIG. 7 is a perspective view of the proximal plate of the plate assembly shown in FIG. 3.

Proximal body 30 also comprises an inside face 44 that extends along the width of body 30. In the depicted embodiment, inside face 44 is planer and arched. In other embodiments, however, inside face 44 can be linear or contoured to have any desired configuration. Outwardly projecting from inside face 44 is a first proximal arm 46A and a spaced apart second proximal arm 46B. As depicted in FIG. 7, first proximal arm 46A has a generally low profile parallel piped configuration that includes a top surface 50 and an opposing bottom surface 52 that extend from a first end 54 to an opposing second end 56. Second end 56 terminates at an end face 58.

An expansion slot 60 extends through first proximal arm 46A from top surface 50 to bottom surface 52 and centrally extends along the length of first proximal arm 46A from first end 54 through end face 58. Expansion slot 60 substantially bisects first proximal arm 46A and can extend all the way to inside face 44 or can terminate at a spaced apart location from inside face 44. In one embodiment, expansion slot extends at least 60% and more commonly at least 70% or 80% of the length of first proximal arm 46A. A threaded bore 62 passes through first proximal arm 46A between top surface 50 and bottom surface 52 at or towards second end 56 and intersects with expansion slot 60. In the depicted embodiment, expansion slot 60 is aligned with the center of threaded bore 62. As will be discussed below in greater detail, threaded bore 62 is configured to threadedly receive first proximal set screw 26A (FIG. 4).

Second proximal arm 46B has substantially the same configuration as first proximal arm 46A. As such, like elements of proximal arms 46A and 46B are identified by like reference characters except that the reference characters for second proximal arm 46B also includes the letter "B". For example, the threaded bore of second proximal arm 46B is referenced as 62B. All disclosure and alternative embodiments discussed with regard to arm 46A are also applicable to arm 46B. Proximal arms 46A and 46B project from inside face 44 at substantially the same angle as the portion of inside face 44 from which the project.

Figure 8:
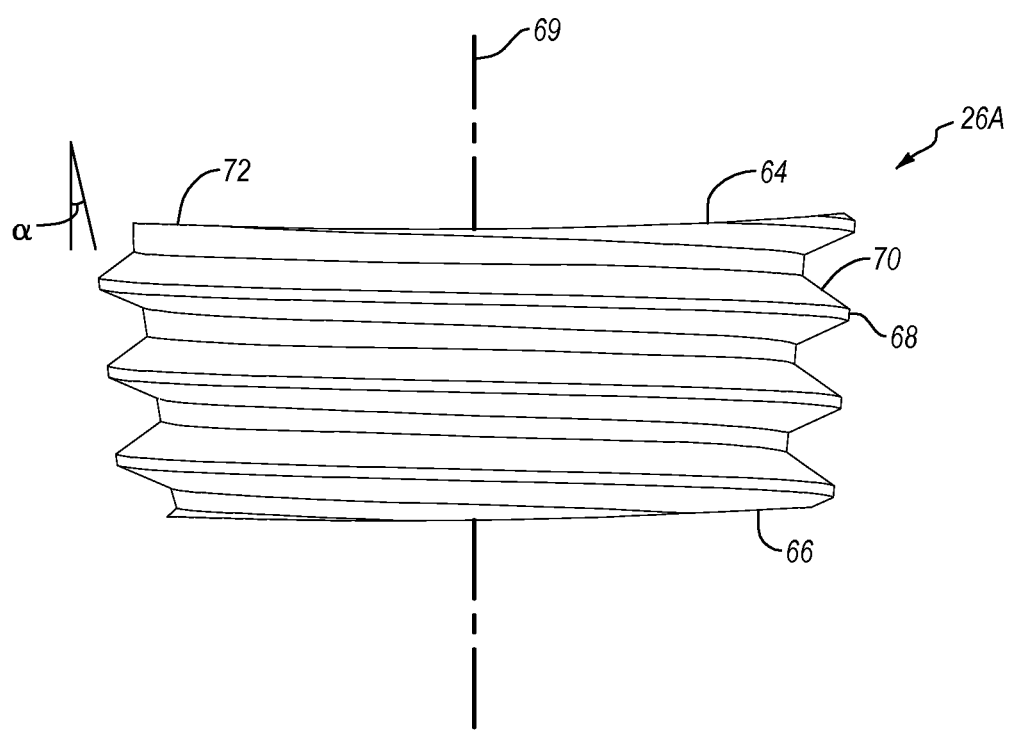
FIG. 8 is an elevated side view of a set screw of the plate assembly shown in FIG. 4.

Threaded bores 62 and 62B are configured to threadedly receive proximal set screws 26A and 26B, respectively. As depicted in FIG. 8, first proximal set screw 26A has a top surface 64 and an opposing bottom surface 66 with an encircling side surface 68 extending therebetween. A central longitudinal axis 69 centrally passes through set screw 26A between top surface 64 and an opposing bottom surface 66. One or more helical threads 70 are formed on side surface 68 and extend from top surface 64 to bottom surface 66. In the depicted embodiment, top surface 64 and bottom surface 66 are both planer. In other embodiments, however, they can be contoured. It is noted that side surface 68 inwardly tapers along the length thereof from top surface 64 to bottom surface 66. As a result, top surface 64 has a larger diameter than bottom surface 66. Side surface 68 is tapered at an angle $\alpha$ measured relative to a line that is parallel to central longitudinal axis 69. The angle $\alpha$ is typically in the range between about 5° to about 40° with about 5° to about 20° being more common. Other angles can also be used.

Top surface 64 has an encircling perimeter edge 72. As depicted in FIG. 3, centrally formed on top surface 64 is a driver engaging feature 74. It is appreciated that driving engaging feature 74 can be any configuration that will permit engaging with a driver for selectively advancing or retracting set screw 26A from threaded bore 62 by rotating set screw 26A. For example, driver engaging feature 74 can be a non-circular recess such as a star shape recess, polygonal recess, slot recess, or the like.

Threaded bore 62 can also be formed with a taper along the length thereof. During use, set screw 26A can be initially threaded into threaded bore 62 (FIG. 4) for coupling therewith without expansion of expansion slot 60. However, the upper end of set screw 26A is larger than the upper end of threaded bore 62. As such, as set screw 26A is further advanced into threaded bore 62, set screw 26A radially outwardly presses against the encircling first proximal arm 46A, thereby causing the lateral expansion of first proximal arm 46A by the expansion of expansion slot 60 and the outward flexing of the bisected halves of first proximal arm 46A. As will be discussed below in greater detail, the outward expansion of first proximal arm 46A is used to secure proximal plate 18 to an adjacent plate. It is appreciated that set screw 26A and threaded bore 62 can have a variety of different configurations that still achieve that same desired expansion as set screw 26A is driven into bore 62. For example, in one embodiment bore 62 can have the same angle taper as set screw 26A but have a smaller diameter. In other embodiments, one of set screw 26A or bore 62 can have a cylindrical configuration while the other is tapered. In still other embodiments, set screw 26A and bore 62 can simply have different tapers to achieve the desired expansion.

Second proximal arm 46B operates with second proximal set screw 26B in the same manner as first proximal arm 46A. Second proximal set screw 26B has the same configuration as first proximal set screw 26A and like elements between set screws 26A and 26B are identified by like reference characters.

Returning to FIG. 3, bone screw 20A comprises a threaded shaft 80 having an enlarged head 82 mounted on the end thereof. Formed on a top surface of head 82 is a driver engaging feature 84. Engaging feature 84 is configured for receiving a driver used for screwing bone screw 20A into bone and can have the same designs and configurations as previously discussed with regard to driver engaging feature 74. Second proximal bone screw 20B has a same configuration as bone screw 20A and like features are identified by like reference characters. Bone screws 20A and 20B are configured to be received within bone screw holes 36 and 38, respectively, so that heads 82 are captured within holes 36 and 38 and can freely pivot therein. This ensures that bone screws 20A and 20B can be placed in a bone at a desired orientation.

Locking element 24A is configured to retain bone screws 20A and 20B once they are received within screw holes 36 and 38. As depicted in FIG. 4, locking element 24A comprises a locking plate 88 having a top surface with a driver engaging feature 90 formed thereon and a bottom surface with a stem 92 projecting therefrom. Locking plate 88 has a pair of cut outs 94A and B formed on opposing sides thereof. Locking element 24A is rotatably coupled to proximal body 30 by stem 92 being received within lock hole 40 and locking plate 88 being received within annular recess 42. Stem 92 can be threaded into lock hole 40. More commonly, however, stem 92 is secured to proximal body 30 so that locking element 24A remains rotatable but cannot become unintentionally detached. For example, the bottom end of stem 92 can be flared outward once received in lock hole 40 so that stem 92 cannot be pulled out of lock hole 40. In other embodiments, an enlarged fastener can be mounted to the bottom end of stem 92 after stem 92 is received in lock hole 40 so that stem 92 cannot be pulled out of lock hole 40. For example, the fastener could be attached by press fitting, welding, screwing using locking threads, or the like. Thus, locking element 24A can be secured like a rivet or other type structure that permits locking element 24A to be secured to proximal body 30 while being rotatable relative thereto.

As depicted in FIG. 3, locking element 24A can be rotated to a first orientation wherein cuts outs 94A and 94B are aligned with screw holes 36 and 38, respectively. In this configuration, bone screws 20A and 20B are free to be advanced down through screw holes 36 and 38 while threading into bone. Once bone screws 20A and 20B are received within screw holes 36 and 38, locking element 24A can be rotated 90° to a second orientation through the use of a driver engaging with driver engaging feature 90 so that a portion of locking plate 88 covers at least a portion of the enlarged head of screws 20A and 20B. In this configuration, locking plate 88 precludes bone screws 20A and 20B from backing out of screw holes 36 and 38. It is appreciated that there are a variety of different locking elements that can be used for locking bone screws 20A and 20B to proximal plate 18.

Figure 4A:
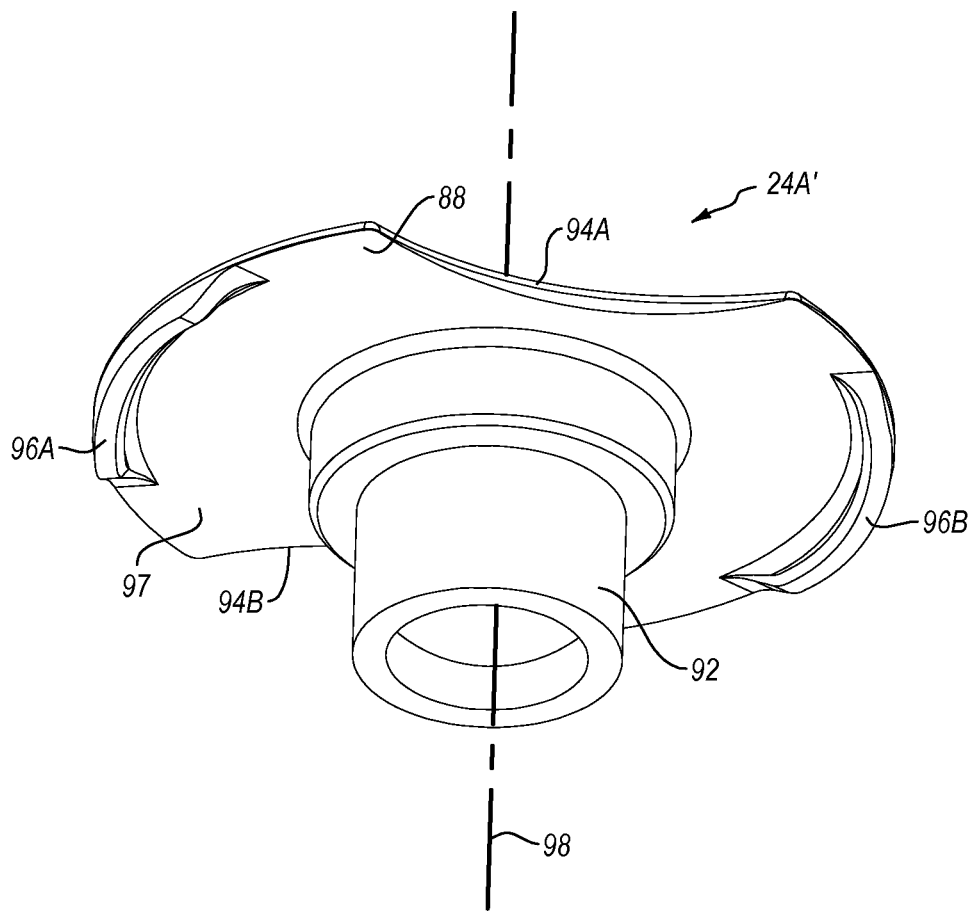
FIG. 4A is a bottom perspective view of an alternative embodiment of a locking element shown in FIG. 4.

Depicted in FIG. 4A is an alternative embodiment of a locking element 24A'. Like elements between locking elements 24A' and 24 are identified by like reference characters. Locking element 24A' is identical to locking element 24 except that elongated projections 96A and 96B project from a bottom surface 97 of locking plate 88 at opposing ends thereof. Projections 96A and 96B are curved along the length thereof so as to have a substantially constant radius measured from a central longitudinal axis 98 extending through stem 92. The opposing ends of each projection 96A and 96B taper toward locking plate 88 in the shape of a ramp.

Figure 4B:
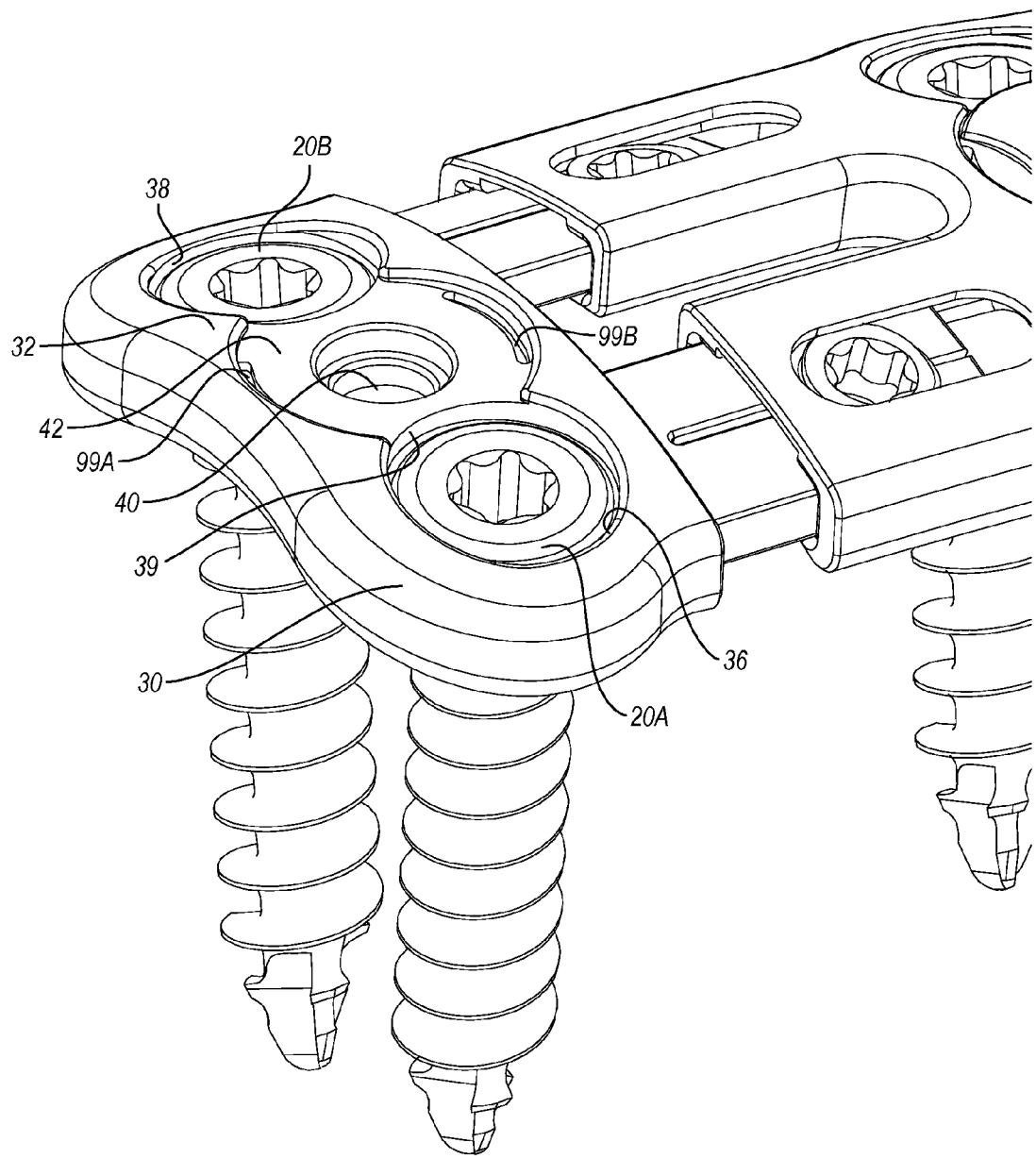
FIG. 4B is a top perspective view of the bone plate shown in FIG. 4 configured to receive the locking element shown in FIG. 4A.

Depicted in FIG. 4B, is a modified annular recess 42 on proximal body 30 into which locking plate 88 (FIG. 4A) is received. Annular recess 42 is formed with grooves 99A and B on opposing ends thereof. Grooves 99A and B have a configuration complementary to projections 96A and 96B and are positioned to receive projections 96A and 96B so as to secure locking element 24A' when locking element 24A' is in the first orientation, i.e., cuts outs 94A and 94B are aligned with screw holes 36 and 38, respectively (FIG. 3). More specifically, locking plate 88 is resiliently flexible and functions to resiliently press projections 96A and 96B into grooves 99A and B when locking element 24A' is in the first orientation.

Figure 4C:
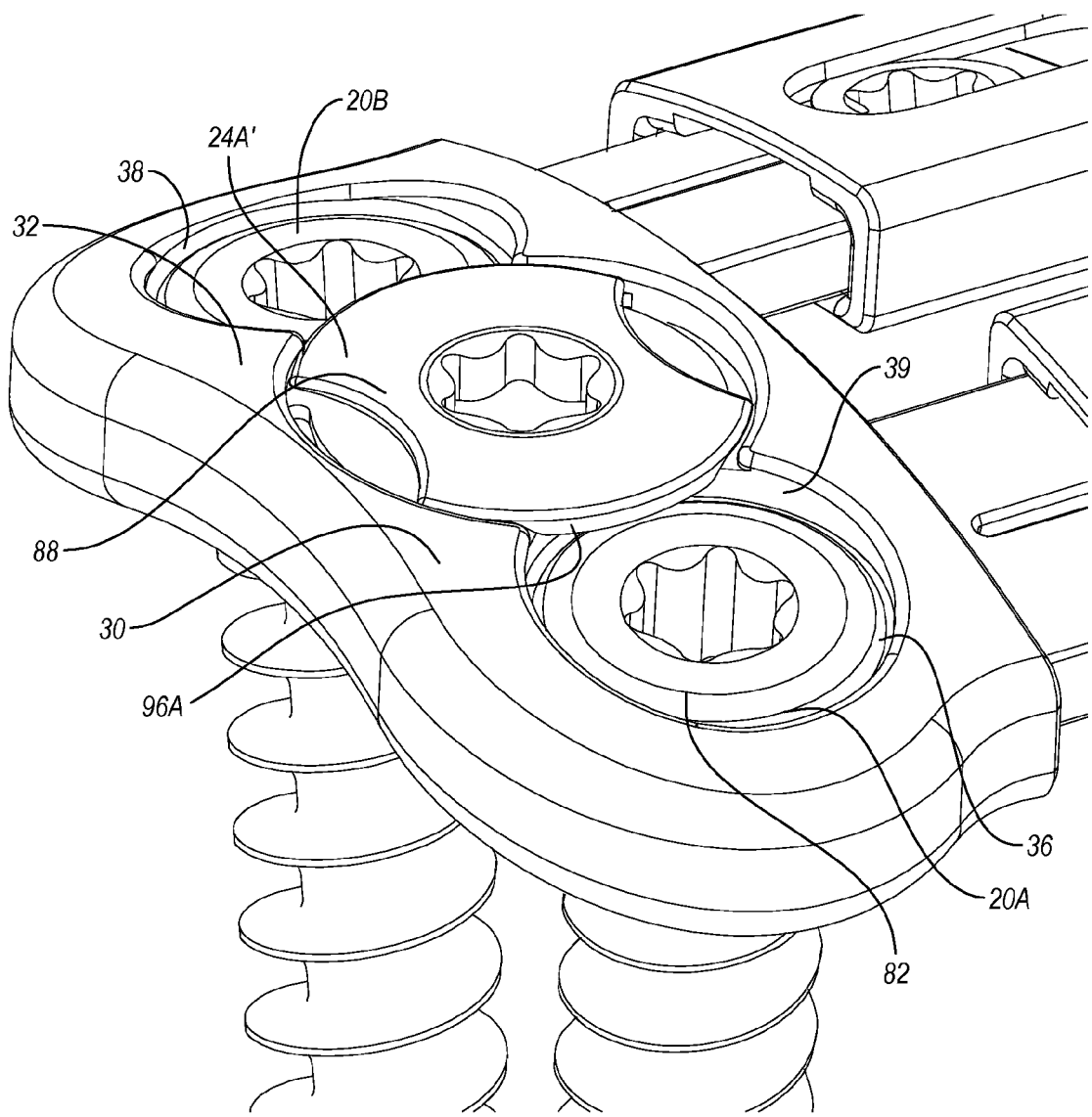
FIG. 4C is a perspective view of the bone plate shown in FIG. 4B having the locking element of FIG. 4A mounted therein and orientated so as to cover two of the bone screws.

Projections 96A and 96B are also formed so that when locking element 24A' is in the second orientation, as depicted in FIG. 4C, projections 96A and 96B are received within bone screw holes 36 and 38. More specifically, bone screws 20A and 20B are configured to be received within bone screw holes 36 and 38 so that heads 82 extend below top surface 32 of proximal body 30. As locking plate 88 is rotated to the second orientation so as to cover a portion of bone screws 20A and 20B, locking plate 88 resiliently presses projections 96A and 96B into bone screw holes 36 and 38 so that the opposing ends of projections 96A and 96B bias against interior surface 39 of bone screw holes 36 and 38, thereby securing locking element 24A' in the second orientation. Accordingly, projections 96A and 96B function to secure locking element 24A' in both the unlocked first orientation and the locked second orientation so that locking element 24A' does not freely rotate unintentionally. This further ensures that bone screws 20A and 20B cannot escape from bone screw holes 36 and 38 once properly locked in place and ensures that bone screw holes 36 and 38 are not unintentionally covered when first inserting bone screws 20A and 20B. In other alternative embodiments, it is appreciated that locking element 24A' would also function with only one of projections 96A and 96B and only one of grooves 99A and B. Likewise, locking element 24A' can also function for covering only a single bone screw. Continuing with FIG. 3, central plate assembly 16 comprises a central plate 100 that can be selectively secured to a bone by first and second central bone screws 20C and 20D. Bone screws 20C and 20D have the same configurations as bone screw 20A and like elements are identified by like reference characters. Rotatably coupled to central plate 100 is a locking element 24B and first and second central set screws 26C and 26D. Set screws 26C and 26D are identical to set screw 26A while locking element 24B is identical to locking element 24A, like features between the different features are identified by like reference characters.

As depicted in FIG. 4, central plate 100 comprises a central body 102 having a top surface 32A and an opposing bottom surface 34A. Central plate 100 has substantially the same compound curvatures front to back and side to side as previously discussed with regard to proximal plate 18. In other embodiments, however, central plate 100 can be flat or have other desired curvatures. First and second central bone screw holes 36A and 38A, having the same configuration as bone screw holes 36 and 38, respectively, extend through central body 102 from top surface 32A to bottom surface 34A. Bone screw holes 36A and 38A receive and retain central bone screws 20C and 20D. A lock hole 40A also passes through central body 102 between top surface 32A and bottom surface 34A at a central location between bone screw holes 36A and 38A. An annular recess 42A is formed on top surface 32A so as to encircle lock hole 40A. Locking element 24B engages with central plate 100 in the same manner as previously discussed with regard to locking element 24A and performs the same function and the same way for retaining bone screws 20C and 20D to central body 102 as locking element 24A. Locking element 24B can also be used with projections 96A and 96B and grooves 99A and B as previously discussed with regard to FIGS. 4A-4C.

Central body 102 has a first side 106 and an opposing second side 108. First side 106 terminates at a first side face 110 from which a first central arm 46C and a spaced apart second central arm 46D outwardly project. Each of arms 46C and 46D have the same configuration as first proximal arm 46A and like elements are identified by like reference characters except that the reference characters of arm 46C include a "C" and the reference characters of arm 46D include a "D".

Figure 9:
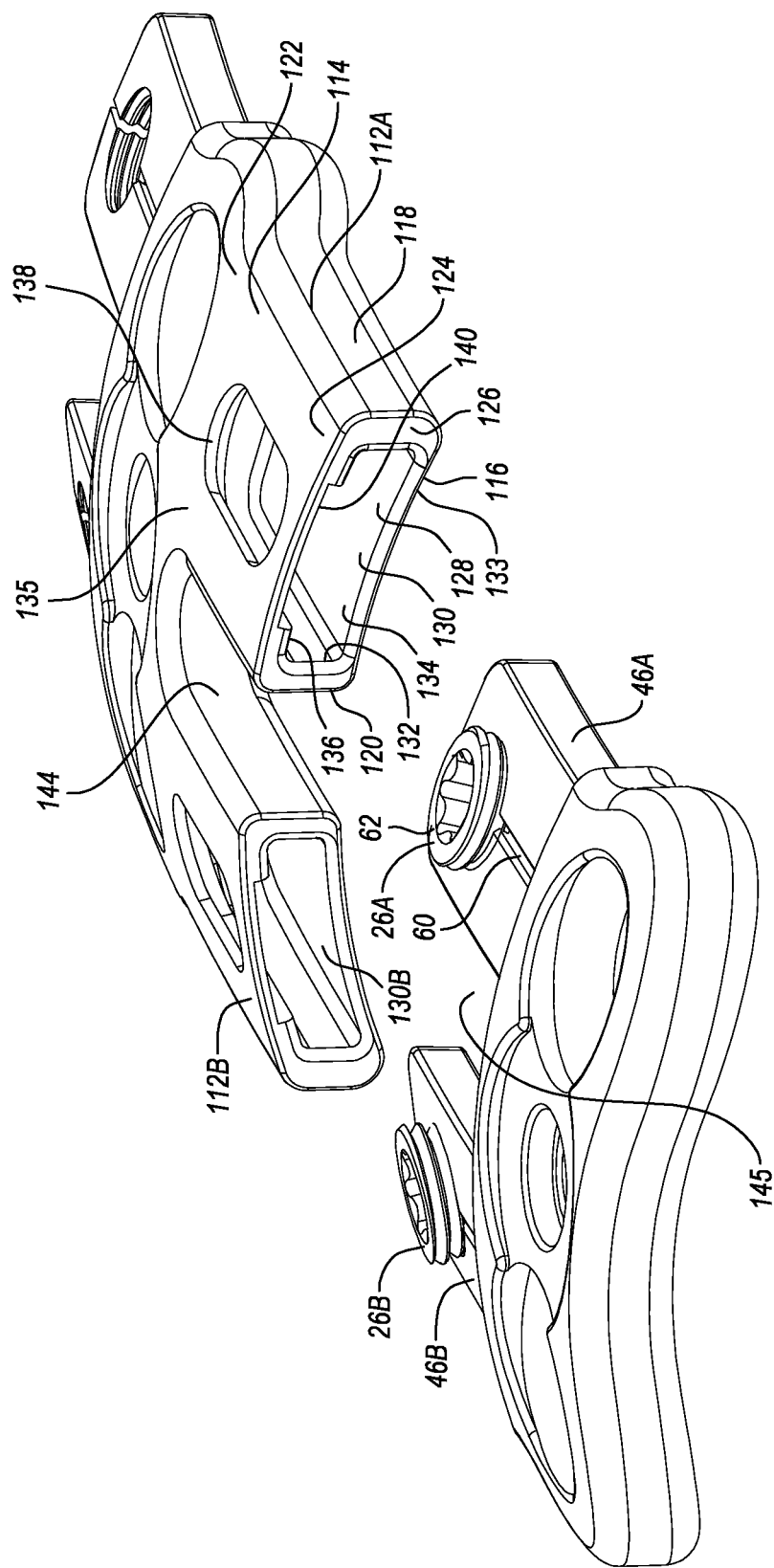
FIG. 9 is an enlarged perspective view of the proximal plate aligned for insertion within the central plate of the plate assembly shown in FIG. 4.

Outwardly projecting from second side 108 of central body 102 is a first central sleeve 112A and a spaced apart second central sleeve 112B. Turning to FIG. 9, sleeve 112A has a top wall 114 and an opposing bottom wall 116 with opposing side walls 118 and 120 extending therebetween. Central sleeve 112A extends between an inside end 122 and an opposing outside end 124. Outside end 124 terminates at an end face 126. First central sleeve 112A also has an interior surface 128 that bounds a first central socket 130. First central socket 130 has a mouth opening 132 formed on end face 126. Top wall 114 has an exterior top surface 135 and an interior ceiling surface 136 while bottom wall 116 has an exterior bottom surface 133 and an interior floor surface 134. An elongated access opening 138 extends through top wall 114 so as to communicate with first central socket 130. Ceiling surface 136 includes a centrally located notch 140 that extends from end face 126 to inside end 122 and is alignment with access opening 138.

First central socket 130 has a configuration and orientation substantially complementarily to first proximal arm 46A so that first proximal arm 46A containing proximal set screw 26A thereon can be slidably received within first central socket 130. When proximal arm 46A is received within socket 130, as depicted in FIG. 3, driver engaging feature 74 on set screw 26A is openly exposed through access opening 138 so that a driver can freely engage set screw 26A for screwing in and out of threaded bore 62.

As also depicted in FIG. 3, the top surface 64 of set screw 26A has a diameter larger than the width of access opening 138. As such, although driver engaging feature 74 is openly exposed through access opening 138 to receive a driver, portions of perimeter edge 72 of top surface 64 of set screw 26A always remain covered by top wall of sleeve 112A, thereby preventing set screw 26A from ever passing out through access opening 138. Accordingly, even if set screw 26A becomes loose, set screw 26A is locked between arm 46 and sleeve 112 so as to prevent unwanted separation therefrom when bone fixation plate assembly 10 is implanted within a patient.

Figure 10:
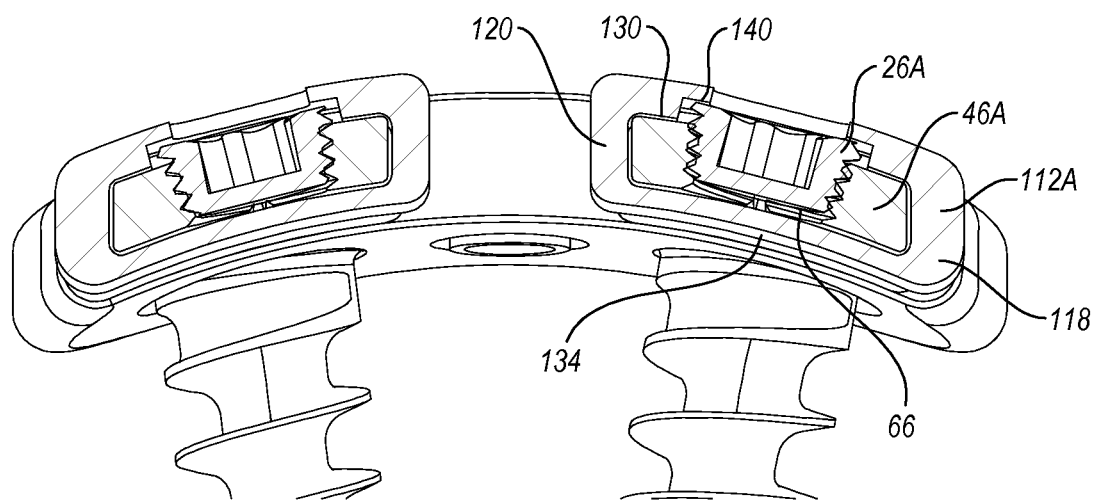
FIG. 10 is a cross sectional side view where two of the plates of the plate assembly are coupled together.

During assembly set screw 26A is received within threaded bore 62 as depicted in FIG. 9. In the depicted embodiment, set screw 26A is sized so that it can be partially threaded into bore 62 without expansion of expansion slot 60 while leaving a portion of the set screw 26A projecting up above first proximal arm 46A. In this configuration, as depicted in FIG. 10, arm 46A can be slid into socket 130 while the upwardly projecting portion of set screw 26A is received within notch 140. Once first proximal arm 46A is advanced to its desired location within socket 130, a driver can be used to advance set screw 26A further into threaded bore 62, thereby laterally expanding first proximal arm 46A so that arm 46A engages against side walls 118 and 120 of sleeve 112A. As a result, first proximal arm 46A is secured within first central socket 130 of sleeve 112A by frictional engagement. It is noted that set screw 26A is configured to be advanced into threaded bore 62 and laterally expand arm 46A within socket 130 so to secure arm 46A therein before bottom surface 66 of set screw 26A contacts floor 134 of sleeve 112A.

Returning to FIG. 9, second central sleeve 112B bounds a second central socket 130B and is substantially identical to first central sleeve 112A. Like elements between sleeves 112A and 112B are identified by like reference characters except that the reference characters of second central sleeve 112B including letter "B". Second central sleeve 112B is oriented complementary to second proximal arm 46B and receives and engages with second proximal arm 46B in the same manner that first central sleeve 112A receives and engages with first proximal arm 46A.

A gap 144 is formed between central sleeves 112A and 112B while a gap 145 is formed between proximal arms 46A and 46B. In the assembled configuration as shown in FIG. 2, gaps 144 and 145 combine to form a window 146 that is openly exposed and passes between proximal plate 18 and central plate 100. Window 146 enables a surgeon to view the underlying bone, spinal disk and/or biological fusion material on which bone fixation plate assembly 10 is mounted during the mounting process.

Returning to FIG. 3, distal plate assembly 14 comprises a distal plate 156 that can be selectively secured to a bone by first and second distal bone screws 20E and 20F. Bone screws 20E and 20F have the same configuration as bone screw 20A and like elements are identified by like reference characters. Rotatably coupled to distal plate 156 is a locking element 24C that is identical to locking element 24A. As depicted in FIG. 4, distal plate 156 comprises a distal body 158 having a top surface 32B and an opposing bottom surface 34B. Distal plate 156 has substantially the same compound curvatures front to back and side to side as previously discussed with regard to proximal plate 18. In other embodiments, however, distal plate 156 can be flat or have other desired curvatures.

First and second distal bone screw holes 36B and 38B extend through distal body 158 from top surface 32B to bottom surface 34B. Bone screw holes 36B and 38B receive and retain central bone screws 20E and 20F in the same manner as previously discussed with Bone screw holes 36 and 38. A lock hole 40B also passes through distal body 158 between top surface 32B and bottom surface 34B at a central location between bone screw holes 36B and 38B. An annular recess 42B is formed on top surface 32B so as to encircle lock hole 40B. Locking element 24C engages with distal plate 158 in the same manner as previously discussed with regard to locking element 24A and performs the same function in the same way for retaining bone screws 20E and 20F to distal body 158 as locking element 24A. Locking element 24C can also be used with projections 96A and 96B and grooves 99A and B as previously discussed with regard to FIGS. 4A-4C.

Distal body 158 has a side 160 from which a first distal sleeve 112C and a spaced apart second distal sleeve 112D outwardly project. Each of sleeves 112C and 112D has the same configuration as first central sleeve 112A and like elements are identified by like reference characters except that the reference characters for sleeve 112C includes a "C" and the reference characters for sleeve 112D include a "D".

In the same manner that proximal plate assembly 12 can couple with central plate assembly 16 by inserting proximal arms 46A and 46B within sockets 130 and 130B, respectively, of central sleeves 112A and 112B, distal plate assembly 14 can be adjustably coupled to central plate assembly 16 by having arms 46C and 46D received within first distal socket 130C and second distal socket 130D of sleeves 112C and 112D, respectively. Again, set screws 26C and 26D can be used to frictionally secure central plate assembly 16 and distal plate assembly 14 together. A gap 144A is formed between sleeves 112C and 112D while a gap 145A is formed between arms 46C and 46D. In the assembled configuration as shown in FIG. 2, gaps 144A and 145A combine to form a window 146C that is openly exposed and passes between distal plate 156 and central plate 100. As with window 146, window 146A enables a surgeon to view the underlying bone on which bone fixation assembly 10 is mounted during the mounting process. Furthermore, as with set screws 26A and 26B, a least a portion of the perimeter edge 72 of set screw 26C and 26D is covered by top wall 114C and 114D of sleeves 112C and 112D, respectively, so that set screws 26C and 26D are captured within sockets 130C and 130D even when set screws 26C and 26D are loose.

Bone fixation plate assembly 10 achieves a number of unique benefits. For example, as previously mentioned bone fixation plate assembly 10 is designed so that all of set screws 26 are captured within sockets 130 of corresponding sleeves 112. This ensures that set screws 26 cannot become disassociated with bone fixation plate assembly 10 when mounted within the body of a patient. Bone fixation plate assembly 10 also has windows 146 and 146A centrally passing through the plate assembly to assist the surgeon in proper alignment and positioning of plate assembly 10.

Furthermore, access openings 138 are elongated so that each of the three separate plates 18, 100, and 156 can be adjustably positioned relative to each other and then locked in place by tightening set screws 26. During the mounting process, each of plates 18, 100, and 156 can be repeatedly adjusted by loosening set screws 26, adjusting the plates and then retightening the set screws 26. Having three separate plates 18, 100, and 156 that can be moveably adjusted relative to each other permits greater flexibility in aligning bone screws 20 so that they can be screwed into the bone at the optimal location. That is, proximal plate 18 and distal plate 156 need not be equally spaced from central plate 100 but can be spaced closer or farther away from each other so that each of bone screws 20 can be placed at the optimal location within a bone. This adjustability has increased benefits where the bone is weak or damaged.

In addition, the present bone fixation plate assembly 10 permits a single plate assembly to be connect to any number of consecutive bones or bone segments. For example, bone fixation plate assembly 10 as depicted comprising three separate plate assemblies 12, 14, and 16 that can each be connect to a separate bone or bone segment. In other embodiments, bone fixation plate assembly 10 can comprise 4, 5, or more plate assemblies by simply inserting further central plate assemblies 16 between proximal plate assembly 12 and distal plate assembly 14 and coupling the plates together in the same manner as previously discussed. By having one continues plate as opposed to multiple separate plates, fewer bone screws are required making the mounting procedure quicker and less damaging to the bone.

Figure 12:
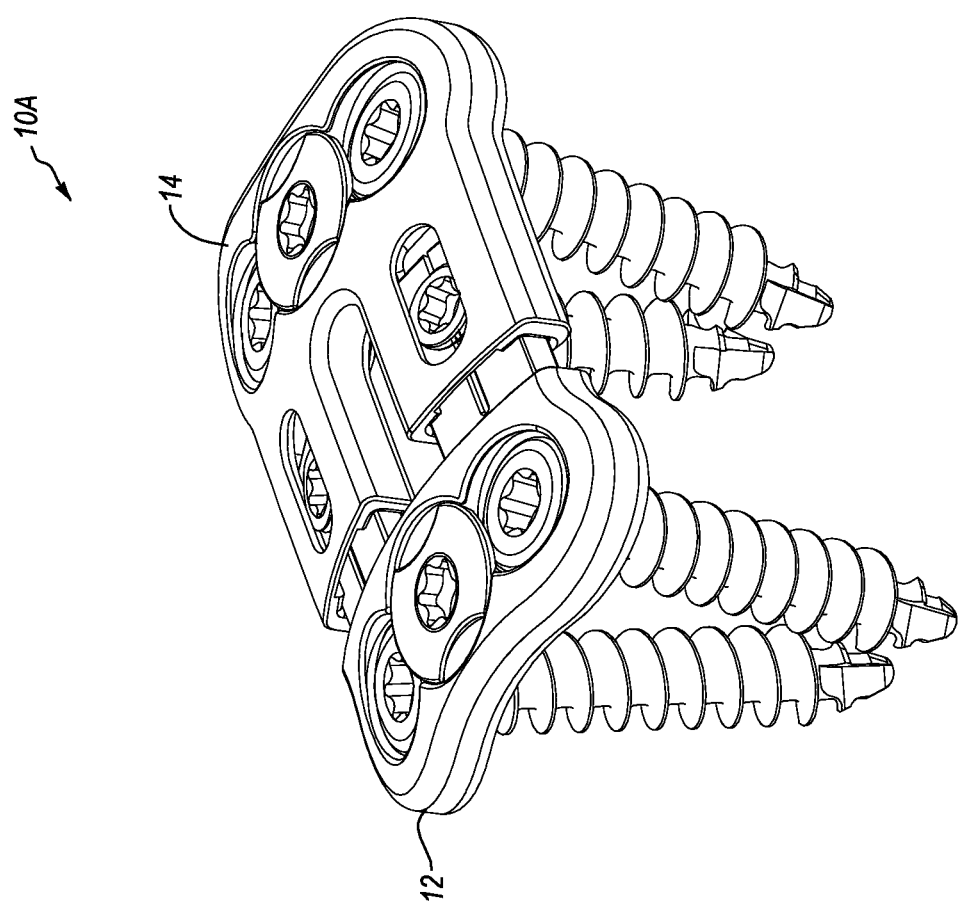
FIG. 12 is a perspective view of the plate assembly shown in FIG. 2 wherein the central plate assembly has been removed.

In another configuration as depicted in FIG. 12, a bone fixation plate assembly 10A can be formed by removing central plate assembly 16 and coupling together proximal plate assembly 12 and distal plate assembly 14 using the same method that proximal plate assembly 12 is coupled with central plate assembly 16. Bone fixation plate assembly 10A can thus be used for securing together two adjacent bones or bone segments.

Furthermore, bone fixation plate assembly 10 can be provided in a kit with a large number of central plate assemblies 16. This permits a surgeon to build a bone fixation plate assembly to a desired configuration based on the needs of a patient. Such a kit thus avoids the need for a surgeon to acquire multiple different plates of different length.

The above benefits of the inventive modular bone fixation plate assembly are particularly advantageous for fusing together adjacent vertebra where the number of vertebra being fused together frequently changes between patients and the vertebra are often weak or damaged.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A bone fixation plate assembly comprising:

(a) a proximal plate assembly comprising:

a proximal plate having a proximal body with a first proximal bone screw hole passing therethrough and a first proximal arm projecting therefrom, the first proximal arm having an elongated expansion slot extending through a portion thereof and a threaded bore formed thereon so as to communicate with the expansion slot; and a first proximal set screw received within the threaded bore of the first proximal arm, the first proximal set screw having a top surface with a driver engaging feature formed thereon and an encircling perimeter edge; and (b) a distal plate assembly comprising:

a distal plate having a distal body with a first distal bone screw hole passing therethrough and a first distal sleeve projecting therefrom, the first distal sleeve having an exterior surface and an interior surface that bounds a first distal socket, the interior surface of the first distal sleeve comprising a ceiling surface, an opposing floor surface, and interior side surfaces that extend therebetween, the first proximal arm being slidably received within the first distal socket, an access opening extending on the first distal sleeve from the exterior surface to the interior surface, the access opening being configured so that the driver engaging feature is accessible through the access opening while at least a portion of the perimeter edge of the first proximal set screw is covered by the first distal sleeve so as to preclude the first proximal set screw from passing out through the access opening.

2. The bone fixation plate assembly as recited in claim 1, wherein the access opening on the first distal sleeve is elongated.

3. The bone fixation plate assembly as recited in claim 1, further comprising an elongated notch formed on the interior surface of the first distal sleeve in alignment with the access opening, the notch having the top surface of the first proximal set screw received therein, the entirety of the first proximal arm being disposed outside of the notch.

4. The bone fixation plate assembly as recited in claim 1, wherein the first proximal set screw has a bottom surface opposite the top surface thereof, the first proximal set screw radially inwardly tapering from the top surface to the bottom surface.

5. The bone fixation plate assembly as recited in claim 1, wherein the expansion slot of the first proximal arm expands when the first proximal set screw is advanced into the threaded bore of the first proximal arm.

6. The bone fixation plate assembly as recited in claim 1, wherein the driver engaging feature comprises a non-circular bore formed on the top surface of the first proximal set screw.

7. The bone fixation plate assembly as recited in claim 1, wherein the first distal sleeve has a top surface on which the access opening is formed and an opposing bottom surface, the bottom surface being disposed so that when the distal plate assembly is horizontally disposed, a vertical axis passing down through the access opening intersects with the bottom surface, the bottom surface being free of any openings through which the first proximal set screw can pass out through.

8. The bone fixation plate assembly as recited in claim 1, further comprising:
   a second proximal arm projecting from the proximal body, the second proximal arm having an elongated expansion slot extending through a portion thereof and a threaded bore formed thereon so as to communicate with the expansion slot;
   a second proximal set screw received within the threaded bore of the second proximal arm; and
   a second distal sleeve projecting from the distal body, the second distal sleeve having an interior surface that bounds a second distal socket, the second proximal arm being slidably received within the second distal socket, the first and second distal sleeves being spaced apart from each other so that an openly exposed window is formed therebetween.

9. The bone fixation plate assembly as recited in claim 1, further comprising an elongated notch being formed on the ceiling surface in alignment with the access opening, the notch being spaced apart from the interior side surfaces and having the top surface of the first proximal set screw received therein.

10. The bone fixation plate assembly as recited in claim 1, wherein the first distal sleeve comprises a top wall though which the access opening is formed, an opposing bottom wall, and a pair of opposing side walls extending therebetween, the access opening being vertically aligned with the bottom wall when the distal plate assembly is horizontally disposed.

11. A bone fixation plate assembly comprising:
   (a) a proximal plate assembly comprising:
   a proximal plate having a proximal body with a first proximal bone screw hole passing therethrough and first and second proximal arms projecting therefrom, each first and second proximal arm having an elongated expansion slot extending through a portion thereof and a threaded bore formed thereon so as to communicate with the corresponding expansion slot; and
   a first proximal set screw received within the threaded bore of the first proximal arm;
   a second proximal set screw received within the threaded bore of the second proximal arm; and
   (b) a distal plate assembly comprising:
   a distal plate having a distal body with a first distal bone screw hole passing therethrough and first and second distal sleeves projecting therefrom, the first distal sleeve bounding a first distal socket having the first proximal arm slidably received therein and the second distal sleeve bounding a second distal socket having the second proximal arm slidably received therein, the first and second distal sleeves being spaced apart from each other so that an openly exposed window is formed therebetween, the first distal sleeve having an interior surface that bounds the first distal socket, the interior surface of the first distal sleeve comprising a ceiling surface, an opposing floor surface, and interior side surfaces that extend therebetween, the interior surface encircling the first proximal arm received within the first distal socket about a longitudinal axis of the first proximal arm.

12. The bone fixation plate assembly as recited in claim 11, wherein the openly exposed window is bounded between the proximal plate and the distal plate.

13. The bone fixation plate assembly as recited in claim 11, further comprising:
   the first proximal set screw having a top surface with a driver engaging feature formed thereon; and
   an access opening extending on the first distal sleeve so as to communicate with the first distal socket, the driver engaging feature of the first proximal set screw being aligned with and accessible through the access opening.

14. The bone fixation plate assembly as recited in claim 11, further comprising:
   first and second distal arms projecting from the distal body on a side of the distal body opposite the first and second distal sleeves, each first and second distal arm having an elongated expansion slot extending through a portion thereof and a threaded bore formed thereon so as to communicate with the corresponding expansion slot; and
   a first distal set screw received within the threaded bore of the first distal arm; and
   a second distal set screw received within the threaded bore of the second distal arm.

15. The bone fixation plate assembly as recited in claim 13, further comprising an elongated notch being formed on the ceiling surface in alignment with the access opening, the notch being spaced apart from the interior side surfaces and having the top surface of the first proximal set screw received therein.

16. The bone fixation plate assembly as recited in claim 13, wherein the first distal sleeve comprises a top wall though which the access opening is formed, an opposing bottom wall, and a pair of opposing side walls extending therebetween, the access opening being vertically aligned with the bottom wall when the distal plate assembly is horizontally disposed.

17. A bone fixation plate assembly comprising:
 (a) a proximal plate assembly comprising:
  a proximal plate having a proximal body with a first proximal bone screw hole passing therethrough and a first proximal arm projecting therefrom, the first proximal arm having an elongated expansion slot extending through a portion thereof and a threaded bore formed thereon so as to communicate with the expansion slot; and
  a first proximal set screw received within the threaded bore of the first proximal arm;
 (b) a distal plate assembly comprising:
  a distal plate having a distal body with a first distal bone screw hole passing therethrough and a first distal sleeve projecting therefrom, the first distal sleeve having an interior surface bounding a first distal socket, the interior surface of the first distal sleeve comprising a ceiling surface, an opposing floor surface, and interior side surfaces that extend therebetween; and
 (c) a central plate assembly comprising:
  a central plate having a central body with a first end and an opposing second end and with a first central bone screw hole passing therethrough, a first central sleeve projecting from the first end of the central body and a first central arm projecting from the second end of the central body, the first central arm having an elongated expansion slot extending through a portion thereof and a threaded bore formed thereon so as to communicate with the expansion slot, the first central sleeve bounding a first central socket; and
  a first central set screw received within the threaded bore of the first central arm;
 wherein the first proximal arm is slidably received within the first central socket and the first central arm is slidably received within the first distal socket.

18. The bone fixation plate assembly as recited in claim 17, further comprising:
 a second proximal arm projecting from the proximal body, the second proximal arm having an elongated expansion slot extending through a portion thereof and a threaded bore formed thereon so as to communicate with the expansion slot, a first proximal set screw being received within the threaded bore of the second proximal arm; and
 a second central sleeve projecting from the first end of the central body and bounding a second central socket, the second proximal arm being received within the second central socket.

19. The bone fixation plate assembly as recited in claim 18, wherein the first and second central sleeves are spaced apart from each other so that an openly exposed window is formed therebetween.

20. The bone fixation plate assembly as recited in claim 17, further comprising:
 the first proximal set screw having a top surface with a driver engaging feature formed thereon; and
 an access opening extending on the first central sleeve so as to communicate with the first central socket, the driver engaging feature of the first proximal set screw being aligned with and accessible through the access opening.

* * * * *